United States Patent [19]

Wegner

[11] Patent Number: 4,547,561

[45] Date of Patent: Oct. 15, 1985

[54] CONSTRUCTION MATERIAL WHICH CAN BE SHAPED UNDER THE INFLUENCE OF HEAT, A PROCESS FOR ITS PREPARATION AND ITS USE

[75] Inventor: Christian Wegner, Cologne, Fed. Rep. of Germany

[73] Assignee: Bayer Aktiengesellschaft, Leverkusen, Fed. Rep. of Germany

[21] Appl. No.: 635,957

[22] Filed: Jul. 27, 1984

[30] Foreign Application Priority Data

Aug. 13, 1983 [DE] Fed. Rep. of Germany ....... 3329392

[51] Int. Cl.$^4$ .............................................. C08G 18/48
[52] U.S. Cl. ...................................... 528/60; 528/66; 528/67; 528/76; 528/77
[58] Field of Search ...................... 528/60, 66, 67, 76, 528/77

[56] References Cited

U.S. PATENT DOCUMENTS 3,755,262 8/1973 Slagel .................................... 528/77

FOREIGN PATENT DOCUMENTS 1560179 1/1980 United Kingdom .
1579860 11/1980 United Kingdom .

*Primary Examiner*—Maurice J. Welsh
*Attorney, Agent, or Firm*—Gene Harsh; Lawrence S. Pope

[57] ABSTRACT

A polyurethane material is disclosed which is hard and has high impact strength at temperatures less than about 45° C. yet can be softened at temperatures above about 60° C. to be manually shapable. This material is obtained by reacting an araliphatic or cycloaliphatic diisocyanate with a polyol component which contains at least 50 wt % of a polyether obtained predominantly from propylene oxide. The polyol component has a number average molecular weight between about 350 and 1000 and an OH number between about 250 and 600. The reaction is conducted at an NCO to OH ratio of between about 0.75:1 and 1.25:1. This material finds utility in the medical field, particularly in forming orthopedic devices, in model construction, as a protective coating, as an impression material, as a decorative material or as a glazing material.

25 Claims, No Drawings

CONSTRUCTION MATERIAL WHICH CAN BE SHAPED UNDER THE INFLUENCE OF HEAT, A PROCESS FOR ITS PREPARATION AND ITS USE

FIELD OF THE INVENTION

The present invention relates to a construction material which is hard and of high impact strength at temperatures up to about 45° C. but can easily be shaped manually above 60° C., a process for its preparation and its use, in particular for orthopedic purposes.

BACKGROUND OF THE INVENTION

The use of materials which can be shaped under the influence of heat in medical technology, in particular in orthopedics, is known.

Thus, for example, German Auslegeschrift (German Published Specification) No. 2,758,216 describes a composition which is applied to a flexible carrier material and which can be shaped after immersion in warm water, and solidifies on cooling. This material is preferably used for producing fixed dressings by being applied in the warmed state in the manner of a plaster bandage. However, at room temperature the material is not hard like a high-impact plastic, but has more the consistency of hard rubber. To produce a fixed dressing from this material, it is therefore necessary to wrap round several layers in order to achieve adequate rigidity of the product. For other uses, such as splints, supports and arch supports, the material does not have the required mechanical properties (in particular rigidity), and its lack of transparency is also a disadvantage.

German Auslegeschrift (German Published Specification) No. 2,618,613 proposes the use of rigid foams which can be shaped under the influence of heat to produce fixed dressings in which splints are inserted. The disadvantage of this material is that it requires steam heated to about 120° C. for softening, for which a special apparatus is necessary. These foams are also unsuitable for producing rigid, thin-walled constructions, since not only do they have a rough, porous surface, but they are also still slightly flexible at room temperature.

However, hard, high-impact, transparent materials which can be shaped under the influence of heat can be prepared, for example, by homopolymerization or copolymerization of methacrylates or acrylates and, if appropriate, other monomers containing vinyl units, such as, for example, acrylonitrile. Such materials are chiefly used in orthopedics. The disadvantage of this class of substance is the temperature > 140° C. which is necessary to render them flexible. This again requires special apparatuses for warming and shaping.

The present invention was thus based on the object of providing a material which is hard, of high impact strength, dimensionally stable and, where relevant, transparent at room temperature but is flexible and can be shaped and molded at temperatures above about 60° C.

BRIEF SUMMARY OF THE INVENTION

The present invention thus relates to a polyurethane-construction material which is hard, of high impact strength, dimensionally stable and, where relevant, transparent at temperatures <45° C., but is flexible and can be shaped and molded at temperatures >60° C., which is characterized in that it is essentially obtainable by reacting (a) at least one araliphatic and/or cycloaliphatic diisocyanate with (b) at least one polyether which is built up predominantly from propylene oxide units and has a molecular weight of about 350–1,000 and an OH number of about 250–600, the NCO/OH ratio being between 0.75:1 and 1.25:1.

The present invention furthermore relates to the use of the construction material according to the invention as an impression material and a support material which can be modelled manually, in particular in the medical field.

DETAILED DESCRIPTION OF THE INVENTION

The diisocyanates used as component (a) are compounds which are liquid and stable to light at room temperature and have at least one cycloaliphatic or aromatic nucleus, but in which the isocyanate groups are not bonded to aromatic carbon.

Examples of such diisocyanates are isophorone diisocyanate, cyclohexane 1,4-diisocyanate, 1-methyl-2,4-diisocyanatocyclohexane, dicyclohexylmethane 4,4'-diisocyanate and xylylene diisocyanate. Isophorone diisocyanate and dicyclohexylmethane 4,4'-diisocyanate are preferred according to the invention. Diisocyanates of the type mentioned which have been modified in a manner which is known per se (biuretized, trimerized, allophanatized, carbodiimidized and the like) can, of course, also be used according to the invention.

The compounds used as component (b) are polyethers which are predominantly built up from propylene oxide units and have a molecular weight of 350 to 1,000, preferably 400 to 800, and an OH number of 250 to 600, preferably 350 to 450. Besides propylene oxide units, the polyethers (b) can contain up to about 40 mol %, preferably less than about 20 mol % and particularly preferably less than about 10 mol %, of other polyether sequences which are known per se (preferably ethylene oxide units). The properties of the materials according to the invention can be controlled in a certain manner by suitable variation of the components containing OH groups. Polyethers of low molecular weight and high OH number provide the property of, for example, a higher crosslinking density. The temperature range for thermal shaping is therefore raised. Propylene oxide polyethers started from trimethylolpropane, pentaerythritol, sorbitol, propylene glycol, glycerol or mixtures thereof are preferred according to the invention. Mixtures of different polyethers can, of course, also be used, as long as they have on average the above-mentioned characteristic data. The polyethers generally have an average OH-functionality of between about 2.0 to 10.0 and preferably between about 2.5 and 6.0.

The polyethers mentioned can also be replaced in part (up to about 50% by weight, preferably less than about 30% by weight and particularly preferably up to about 20% by weight) by other components containing OH groups. Components which may be mentioned in particular here are tetrahydrofuran polymers, polycaprolactonepolyols and polyesters containing OH groups, especially if they contain phthalic acid or adipic acid units. In this case also, the mixture of all the compounds containing OH groups have an average molecular weight of about 350 to 1,000 and an average OH number of about 250 to 600. The molar ratio of all the NCO groups to all the OH groups in the preparation of the construction materials according to the invention is about 0.75–1.25:1, preferably about 0.9–1.1:1 and especially about 1:1.

The materials according to the invention are clear, transparent and of high impact strength at room temperature. They do not yellow under the influence of light and no turbidity caused by absorption of moisture occurs even on prolonged contact with cold or hot water. The materials are rubbery-soft at temperatures >60° C. and can be subjected to any desired shaping process, such as, for example, bending, rolling or folding. However, it is surprising and of significance for the handling of these materials that, in the warmed state, that is to say the state in which they can be shaped, the materials can be cut like a textile substance or a felt material with conventional scissors or other simple cutting tools, clean edges being obtained. In contrast, in the cooled state the material can also be subjected to the customary methods of working, such as, for example, boring, turning, grinding or milling.

The materials according to the invention are prepared by the customary methods in the polyurethane industry. Thus for example, it is possible to mix the components homogeneously and to introduce the mixture into a mold and harden it at elevated temperature. Hardening is preferably carried out in the presence of catalysts which are known per se, organotin compounds, such as, for example, tin octoate or dibutyl-tin dilaurate, being particularly suitable.

The method described can also be varied in many respects. Thus, instead of the monomeric starting components (a) and (b), that is to say the diisocyanate mixture and the polyol or polyol mixture, it is also possible to use prepolymers with free terminal OH or NCO groups formed from these components. A proportion of the NCO groups of the diisocyanates used can also be subjected to other modification reactions known in isocyanate chemistry, such as, for example, biuretization, trimerization, carbodiimidization, urea formation and allophanatization. Continuous production of sheets or bars is likewise possible if the process is carried out with a metering and mixing apparatus, to which is connected a heated belt on which the composition hardens.

Like other plastics, the materials according to the invention can also be colored, lacquered or provided with inorganic or organic fillers in a manner which is known per se.

Besides the medical field, in particular orthopedics, the use of the materials according to the invention is suitable in all cases where materials which have good mechanical properties and can be shaped and cut in a simple manner are required, such as, for example, as construction materials for models, fixing elements, decoration materials and transparent coverings, as an impression material or as an imitation glass material for glazing.

The invention is further illustrated, but is not intended to be limited by the following examples in which all parts and percentages are by weight unless otherwise specified.

EXAMPLES

Example 1

100 parts of a polypropylene oxide polyether started from trimethylolpropane (OH number 375, molecular weight 450) are homogeneously mixed with 73 parts of isophorone diisocyanate and 0.01% of tin-II octoate and the mixture is degassed and hardened at 80° C. to a sheet 4 mm thick. A transparent, optically pure, colorless, high-impact material which can easily be shaped or cut manually at 65° C. is obtained.

Example 2

The procedure followed is as described in Example 1, but 86.5 g of dicyclohexylmethane 4,4'-diisocyanate are used as the isocyanate component. A material as in Example 1 which can be shaped or cut manually at 75° C. is obtained.

Example 3

63 parts of a propylene oxide polyether started from sorbitol and propylene glycol (OH number 480, molecular weight 500) and 37 parts of a propylene oxide polyether started from propylene glycol (OH number 112, molecular weight 1,000) are mixed with 68 parts of isophorone diisocyanate and the mixture is hardened as described in Example 1. A material analogous to that in Example 1 but which can be shaped or cut manually only at 80° C. is obtained.

Example 4

75 parts of a propylene oxide polyether started from sorbitol and propylene glycol (OH number 480, molecular weight 500) and 25 parts of a propylene oxide polyether started from propylene glycol (OH number 112, molecular weight 1,000) are mixed with 76.9 parts of isophorone diisocyanate and the mixture is hardened as described in Example 1. A material analogous to that in Example 1 but which can be shaped or cut manually only at 90° C. is obtained.

Example 5

50 parts of the propylene oxide polyether used in Example 1, 20 parts of a polyester built up from phthalic anhydride and ethylene glycol (OH number 280), 47.7 parts of isophorone diisocyanate and 0.6 parts of dibutyl-tin dilaurate are mixed homogeneously and the mixture is hardened as described in Example 1. A material analogous to Example 1 which can easily be shaped at 85° C. is obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polyurethane constructional material which is hard and has high impact strength at temperatures below about 45° C. but is softened to a manually shapable state by exposure to temperatures in excess of about 60° C. comprising the reaction product of
    a) an isocyanate component comprising at least one diisocyanate which:
        i) contains at least one cycloaliphatic or aromatic residue in its molecular structure; and
        ii) has both of its isocyanate groups bound to other than an aryl carbon atom; with
    b) a polyol component comprising at least one polyether which:
        i) is built up predominantly from propylene oxide units;
        ii) has a number average molecular weight of between about 350 and 1000; and
        iii) has an OH number between about 250 and 600, said reaction product being synthesized using an NCO to OH ratio of between about 0.75:1 and 1.25:1.

2. The material of claim 1 wherein the NCO to OH ratio used in synthesizing the reaction product is between about 0.9:1 and 1.1:1.

3. The material of claim 1 wherein the isocyanate component also contains biuretized, trimerized or carbodiimidized diisocyanate.

4. The material of claim 1 wherein at least one diisocyanate is selected from the group consisting of isophorone diisocyanate, dicyclohexane-4,4'-diisocyanate, xylylene diisocyanate and mixtures thereof.

5. The material of claim 1 or 2 or 3 or 4 wherein the polyol component is a polyether comprising at least about 60 mol percent of propylene oxide residues.

6. The material of claim 5 wherein the polyether comprises at least about 80 mol percent propylene oxide residues.

7. The material of claim 1 or 2 or 3 or 4 wherein the polyol component is a polyether started on an initiator selected from the group consisting of propylene glycol, glycerol, trimethylol propane, pentaerythritol, sorbitol and mixtures thereof.

8. The material of claim 7 wherein the polyether comprises at least about 60 mol percent propylene oxide residues.

9. The material of claim 8 wherein the polyether comprises at least about 80 mol percent propylene oxide residues.

10. The material of claim 1 or 2 or 3 or 4 wherein the polyether
    (a) has a number average molecular weight of between about 400 and 800; and
    (b) has an OH number between about 350 and 450.

11. The material of claim 10 wherein the polyether comprises at least about 60 mol percent of propylene oxide residues.

12. The material of claim 1 or 2 or 3 or 4 wherein the polyol component comprises a mixture of polyethers which give the mixture the average properties of
    (a) a number average molecular weight between about 350 and 1000; and
    (b) an OH number between about 250 and 600.

13. The material of claim 12 wherein
    (a) the number average molecular weight is between about 400 and 800; and
    (b) the OH number is between about 350 and 450.

14. The material of claim 1 or 2 or 3 or 4 wherein
    (a) up to about 500 mol percent of the polyol component comprises hydroxyl bearing compounds other than polyethers; and
    (b) the polyol component has:
        (i) a number average molecular weight of between about 350 and 1000; and
        (ii) an average OH number between about 250 and 600.

15. The material of claim 14 wherein
    (a) the number average molecular weight is between about 400 and 800; and
    (b) the OH number is between about 350 and 450.

16. The polyurethane constructional material which is hard and has high impact strength at temperatures below about 45° C. but is softened to a manually shapable state by exposure to temperatures in excess of about 60° C. comprising the reaction product of
    (a) a diisocyanate selected from the group consisting of isophorone diisocyanate, dicyclohexane-4,4'-diisocyanate, xylylene diisocyanate and mixtures thereof, and
    (b) at least one polyether
        (i) comprising at least about 80 mol percent of propylene oxide residues;
        (ii) started on an initiator selected from the group consisting of propylene glycol, glycerol, trimethylol propane, pentaerythritol, sorbitol and mixtures thereof;
        (ii) having a number average molecular weight between about 400 and 800; and
        (iv) having an OH number between about 350 and 450, said reaction product being synthesized using an NCO to OH ratio of between about 0.9:1 and 1.25:1.

17. A process for the preparation of a polyurethane constructional material which is hard and has a high impact strength at temperatures below about 45° C. but is softened to a manually shapable state by exposure to temperatures in excess of about 60° C. comprising reacting
    (a) an isocyanate component comprising at least one diisocyanate which:
        (1) contains at least one cycloaliphatic or aromatic residue in its molecular structure; and
        (2) has both of its isocyanate groups bound to other than an aryl carbon atom; with
    (b) a polyol component comprising
        (1) at least one polyether which
            (i) is built up predominantly from propylene oxide units;
            (ii) has a number average molecular weight of between about 350 and 1000; and
            (iii) has an OH number between about 250 and 600; and
        (2) optionally up to 50 wt. percent, based on the total weight of the polyol component, of other OH bearing compounds so selected that the polyol component has on average
            (i) number average molecular weight between about 350 and 1000; and
            (ii) an OH number between about 250 and 600, said reaction being conducted in one or several stages such that the overall NCO to OH ratio is between about 0.75:1 and 1.25:1 under conditions suitable for the formation of a polyurethane.

18. A process for the formation of an orthopedic device comprising
    (a) forming a material which is hard and has high impact strength at temperatures below about 45° C. but is softened to a manually shapable state by exposure to temperatures above about 60° C. in accordance with claim 17;
    (b) heating or maintaining the material obtained from step (a) at a temperature above about 60° C. until it is shaped to the desired configuration; and
    (c) allowing the shaped material to cool to below about 45° C.

19. A process for the preparation of rigid plastic articles having good impact strength and displaying hardness similar to that obtainable from homopolymers of methyl methacrylate comprising
    (a) forming a material which is hard and has high impact strength at temperatures below about 45° C. but is softened to a manually shapable state by exposure to temperatures above about 60° C. in accordance with claim 17;

(b) forming this material into the desired configuration at a temperature above about 60° C.; and (c) allowing the shaped material to cool to below about 45° C.

20. The process of claim 19 wherein the material is transparent and is utilized as a glazing material.

21. The process of claim 19 wherein the material is formed by impressing it with a rigid article.

22. The process of claim 19 wherein the material is formed into a decorative configuration.

23. The process of claim 19 wherein the material is formed into a model of a larger or smaller article.

24. The process of claim 19 wherein the material is formed into a protective covering.

25. A process for the formation of an orthopedic device comprising (a) forming a material which is hard and has a high impact strength at temperatures below 45° C. but is softened to a manually shapable state by exposure to temperatures above 60° C. by reacting (I) an isocyanate component comprising at least one diisocyanate which:

(i) contains at least one cycloaliphatic or aromatic residue in its molecular structure; and (ii) has both of its isocyanate groups bound to other then an aryl carbon atom; with (II) a polyol component comprising:

(i) at least one polyether which is built up predominantly from polypropylene oxide units, has a number average molecular weight from about 350 and 1000, and has an OH number between about 250 and 600;

(ii) optionally up to 50 weight percent, based on the total weight percent of the polyol component, of other OH bearing compounds so selected that the polyol component has an average number average molecular weight between 350 and 1000; and an OH number between 250 and 600, said reaction being conducted in one or several stages such that the overall NCO:OH ratio is between about 0.75:1 and 1.25:1 under conditions suitable for the formation of a polyurethane, (b) casting this reaction mixture into the form of a sheet, (c) heating this sheet material to a temperature in excess of 60° C., (d) conforming this heated sheet material to the portion of the human or animal body to be supported or immobilized by the orthopedic material, (e) allowing this conformed material to cool down to a temperature below 45° C., and affixing or securing the cooled sheet material to the body portion to which it has been conformed.

* * * * *